United States Patent
Dacosta et al.

(10) Patent No.: US 10,470,900 B2
(45) Date of Patent: Nov. 12, 2019

(54) IMPLANTS, DEVICES, SYSTEMS, KITS AND METHODS OF IMPLANTING

(71) Applicant: Paragon 28, Inc., Englewood, CO (US)

(72) Inventors: Albert Dacosta, Lone Tree, CO (US);
Thomas Chang, Santa Rosa, CA (US);
Frank S. Bono, Castle Rock, CO (US);
Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 148 days.

(21) Appl. No.: 15/186,005

(22) Filed: Jun. 17, 2016

(65) Prior Publication Data

US 2017/0360577 A1 Dec. 21, 2017

(51) Int. Cl.
*A61F 2/46* (2006.01)
*A61F 2/42* (2006.01)
(Continued)

(52) U.S. Cl.
CPC ............ *A61F 2/4684* (2013.01); *A61B 17/68* (2013.01); *A61B 17/8095* (2013.01);
(Continued)

(58) Field of Classification Search
CPC ........ A61F 2/4684; A61F 2/46; A61F 2/4225; A61F 2/4606; A61F 2/4455; A61F 2/446; A61F 2/4601; A61F 2/4611; A61F 2002/4615; A61F 2002/4623; A61F 2002/4624; A61F 2002/4687;
(Continued)

(56) References Cited

U.S. PATENT DOCUMENTS

| | | | | |
|---|---|---|---|---|
| 4,566,466 A | * | 1/1986 | Ripple | A61B 17/15 606/102 |
| 4,834,757 A | * | 5/1989 | Brantigan | A61B 17/1604 623/17.11 |

(Continued)

FOREIGN PATENT DOCUMENTS

WO 20120100054 A1 7/2012

OTHER PUBLICATIONS

Extended European Search Report issued in corresponding European Patent Application No. 17176459.0 dated Dec. 20, 2017.

*Primary Examiner* — Alvin J Stewart
(74) *Attorney, Agent, or Firm* — Heslin Rothenberg Farley & Mesiti PC

(57) ABSTRACT

A distraction kit including at least one trial insert, at least one handle for coupling to the at least one trial insert, a correction indication guide, and at least one implant. A method for performing a distraction arthrodesis including inserting at least one trial insert into a joint and selecting a trial insert of the at least one trial insert for correction of the joint in a first plane. The method also including rotating the selected trial insert in a medial-lateral direction for correction of the joint in a second plane and selecting the needed correction in the first plane and the second plane. The method further including marking at least one bone for the selected correction. Then, marking the implant with the correction indication guide to achieve proper placement of the implant and joint correction replication from the desired trial positioning. Implants, devices, and systems are also disclosed.

17 Claims, 18 Drawing Sheets

(51) Int. Cl.
  *A61B 17/80* (2006.01)
  *A61B 17/68* (2006.01)
  *A61B 17/02* (2006.01)
  *A61B 17/00* (2006.01)
  *A61F 2/30* (2006.01)
  *A61B 17/56* (2006.01)

(52) U.S. Cl.
  CPC .......... *A61F 2/4225* (2013.01); *A61F 2/4606* (2013.01); *A61B 17/025* (2013.01); *A61B 2017/00407* (2013.01); *A61B 2017/565* (2013.01); *A61F 2002/30115* (2013.01); *A61F 2002/4223* (2013.01); *A61F 2250/0097* (2013.01)

(58) Field of Classification Search
  CPC .. A61F 2002/30607; A61F 2002/30616; A61F 2002/30617; A61B 17/025; A61B 2017/0256; A61B 2017/0275; A61B 2017/0268
  See application file for complete search history.

(56) References Cited

U.S. PATENT DOCUMENTS

| | | | | |
|---|---|---|---|---|
| 5,690,636 A * | 11/1997 | Wildgoose | ......... | A61B 17/1604 606/100 |
| 5,976,147 A * | 11/1999 | LaSalle | .............. | A61B 17/1604 606/102 |
| 6,436,102 B1 * | 8/2002 | Ralph | ................. | A61B 17/025 606/90 |
| 6,942,670 B2 * | 9/2005 | Heldreth | ............ | A61B 17/1735 606/102 |
| 6,984,245 B2 * | 1/2006 | McGahan | ............. | A61F 2/4465 623/17.11 |
| 7,172,599 B2 * | 2/2007 | Steffensmeier | ........ | A61B 90/06 33/512 |
| 7,247,169 B1 * | 7/2007 | Lo | ......................... | A61F 2/4684 606/279 |
| 7,309,363 B2 * | 12/2007 | Dietz | .................... | A61F 2/4657 606/102 |
| 7,632,314 B2 * | 12/2009 | Dietz | .................... | A61F 2/4657 623/20.33 |
| 8,083,746 B2 * | 12/2011 | Novak | ................... | A61B 17/15 606/87 |
| 8,632,547 B2 * | 1/2014 | Maxson | ............... | A61B 17/151 606/88 |
| 8,945,231 B2 * | 2/2015 | Young | .................... | A61F 2/389 623/20.32 |
| 8,968,412 B2 * | 3/2015 | Wogoman | ............. | A61F 2/4684 623/20.15 |
| 8,979,847 B2 * | 3/2015 | Belcher | ................. | A61B 17/155 606/79 |
| 9,095,453 B2 * | 8/2015 | Ries | ...... | A61B 17/1764 |
| 9,144,495 B2 * | 9/2015 | Lin | ....... | A61F 2/4684 |
| 9,149,206 B2 * | 10/2015 | Claypool | .............. | A61F 2/4657 |
| 9,277,965 B2 * | 3/2016 | Dietz | .................... | A61F 2/4657 |
| 9,398,928 B2 * | 7/2016 | Chavarria | .............. | A61B 17/88 |
| 9,693,882 B2 * | 7/2017 | Lomeli | ................ | A61F 2/4684 |
| 9,763,807 B2 * | 9/2017 | Claypool | .............. | A61F 2/4684 |
| 9,770,345 B2 * | 9/2017 | Belcher | ................. | A61F 2/4684 |
| 9,883,948 B2 * | 2/2018 | Chavarria | .......... | A61B 17/8061 |
| 2002/0082607 A1 * | 6/2002 | Heldreth | ............ | A61B 17/1735 606/102 |
| 2003/0139812 A1 * | 7/2003 | Garcia | ................. | A61B 17/025 623/17.11 |
| 2004/0133279 A1 * | 7/2004 | Krueger | ............. | A61B 17/7062 623/17.16 |
| 2005/0143173 A1 * | 6/2005 | Barney | ................... | A63F 13/06 463/37 |
| 2005/0251147 A1 | 11/2005 | Novak | | |
| 2006/0111790 A1 * | 5/2006 | Dietz | .................... | A61F 2/4657 623/20.32 |
| 2008/0058946 A1 * | 3/2008 | Dietz | .................... | A61F 2/4657 623/20.32 |
| 2009/0105824 A1 * | 4/2009 | Jones | ...................... | A61F 2/447 623/17.16 |
| 2009/0132045 A1 * | 5/2009 | Lafosse | ................. | A61F 2/4684 623/14.12 |
| 2010/0125337 A1 * | 5/2010 | Grecco | ................. | A61F 2/4684 623/20.16 |
| 2010/0249777 A1 * | 9/2010 | Sherman | ............. | A61B 5/1107 606/53 |
| 2010/0292801 A1 * | 11/2010 | Hansell | .................... | A61F 2/442 623/17.16 |
| 2011/0213376 A1 | 9/2011 | Maxson et al. | | |
| 2015/0335367 A1 | 11/2015 | Austin et al. | | |
| 2015/0342757 A1 * | 12/2015 | Lomeli | ................ | A61F 2/4684 623/17.16 |
| 2016/0058571 A1 * | 3/2016 | McLaughlin | ........... | A61F 2/442 623/17.16 |
| 2017/0065427 A1 * | 3/2017 | Songer | ................. | A61F 2/4455 |

* cited by examiner

250

250

IMPLANTS, DEVICES, SYSTEMS, KITS AND METHODS OF IMPLANTING

FIELD OF THE INVENTION

The present invention relates generally to general surgery, orthopaedic implants used for achieving bone fusion. More specifically, but not exclusively, the present invention relates to implants, devices, systems, kits and methods for implanting for bone alignment.

BACKGROUND OF THE INVENTION

Currently available subtalar distraction arthrodesis procedures and implants do not allow for the desired correction and restoration of function. Thus, new methods, implants, and systems are needed to allow for desired correction of the subtalar joint.

SUMMARY OF THE INVENTION

Aspects of the present invention provide implants, devices and methods for implanting for bone alignment.

In one aspect, provided herein is a distraction kit. The distraction kit includes at least one trial insert, at least one handle for coupling to the at least one trial insert, a correction indication guide, and at least one implant.

In another aspect, provided herein is a surgical method for performing a distraction arthrodesis. The method including inserting at least one trial insert of a trial inserter system into a joint and selecting a trial insert of the at least one trial insert for correction of the joint in a first plane. The method also including rotating the selected trial insert in a medial and lateral direction for correction of the joint in a second plane and selecting the needed correction in the first plane and the second plane. The method further including ensuring that the distraction height and corresponding fit is adequate and marking at least one bone of the joint for the selected correction.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein is one embodiment of an implant, devices, systems, and kits for bone alignment. Further, a surgical method for using the implant, devices and systems is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Similarly, positions or directions may be used herein with reference to anatomical structures or surfaces. For example, as the current devices and methods are described herein with reference to use with the bones of the foot, the bones of the foot, ankle and lower leg may be used to describe the surfaces, positions, directions or orientations of the devices, instrumentation and methods. Further, the devices and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices and methods, and the aspects, components, features and the like thereof, described herein with respect to the right foot may be mirrored so that they likewise function with the left foot. Further, the implants, devices and methods, and the aspects, components, features and the like thereof, disclosed herein are described with respect to the foot for brevity purposes, but it should be understood that the devices and methods may be used with other bones of the body having similar structures, for example the upper extremity, and more specifically, with the bones of the wrist, hand, and arm.

Figure 3:
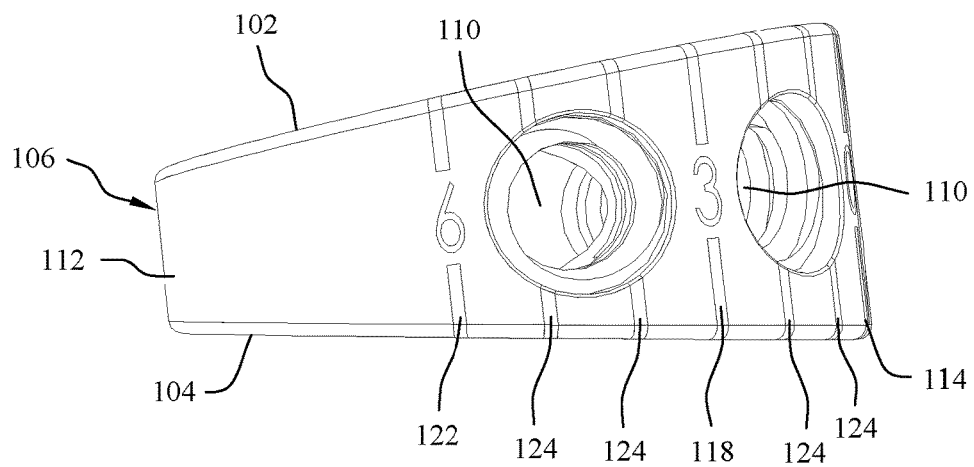
FIG. 3 is a first side view of the trial insert of FIG. 1, in accordance with an aspect of the present invention.
Figure 4:
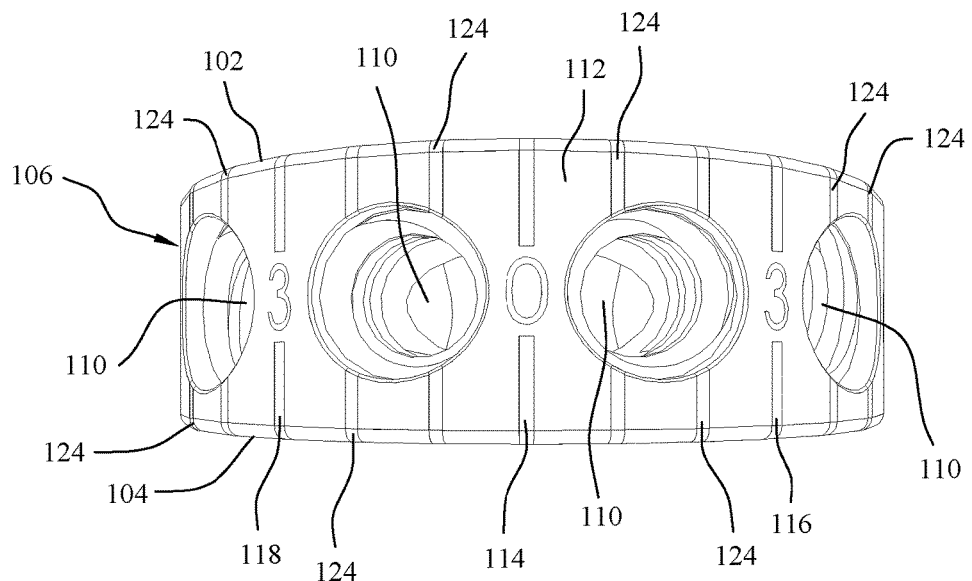
FIG. 4 is a front view of the trial insert of FIG. 1, in accordance with an aspect of the present invention.
Figure 5:
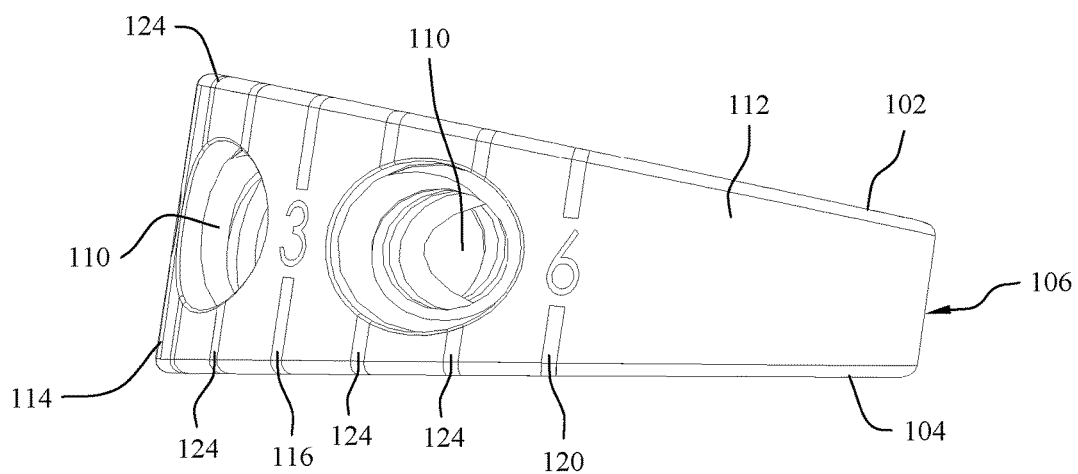
FIG. 5 is a second side view of the trial insert of FIG. 1, in accordance with an aspect of the present invention.

Referring to the drawings, wherein like reference numerals are used to indicate like or analogous components throughout the several views, and with particular reference to FIGS. 1-5, there is illustrated one embodiment of a trial insert 100. The trial insert 100 may include a top surface 102, a bottom surface 104 and a body portion 106 extending between the top surface 102 and the bottom surface 104. The top surface 102 may be angled with respect to the bottom surface 104, as shown in FIGS. 3 and 5. The trial insert 100 may also include an opening 108 extending from the top surface 102 to the bottom surface 104 through the body portion 106. In addition, the trial insert 100 may include at least one hole 110 extending into the body portion 106 from the exterior surface 112 of the body portion 106 toward the opening 108. The at least one hole 110 may be, for example, threaded. As shown in FIGS. 1-5, the trial insert 100 may include, for example, four holes 110.

Figure 1:
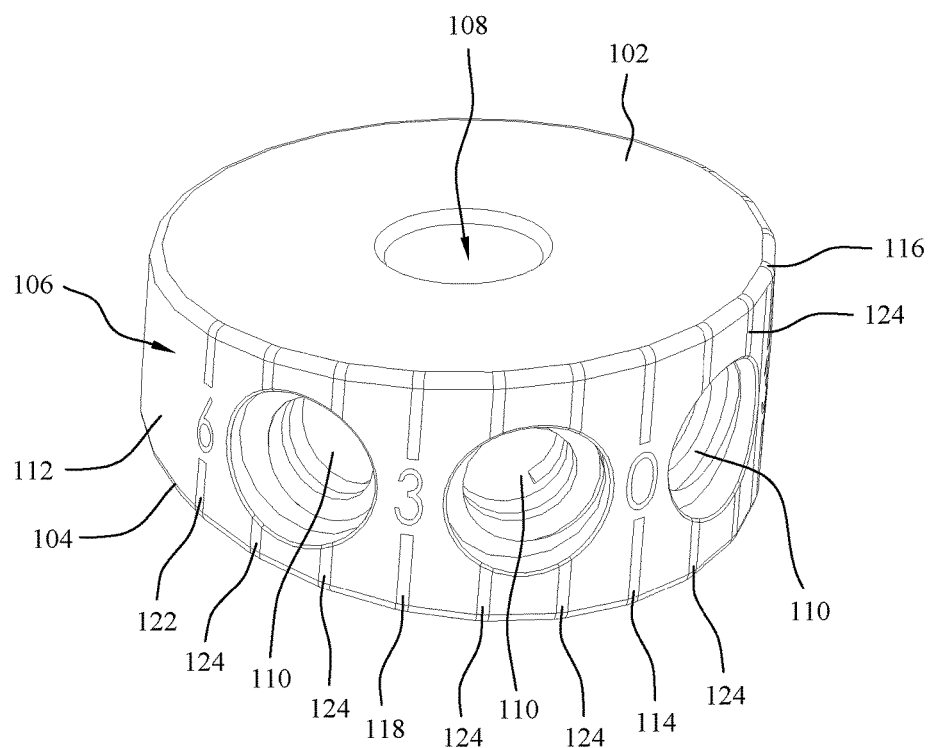
FIG. 1 is a perspective view of one embodiment of a trial insert, in accordance with an aspect of the present invention.
Figure 2:
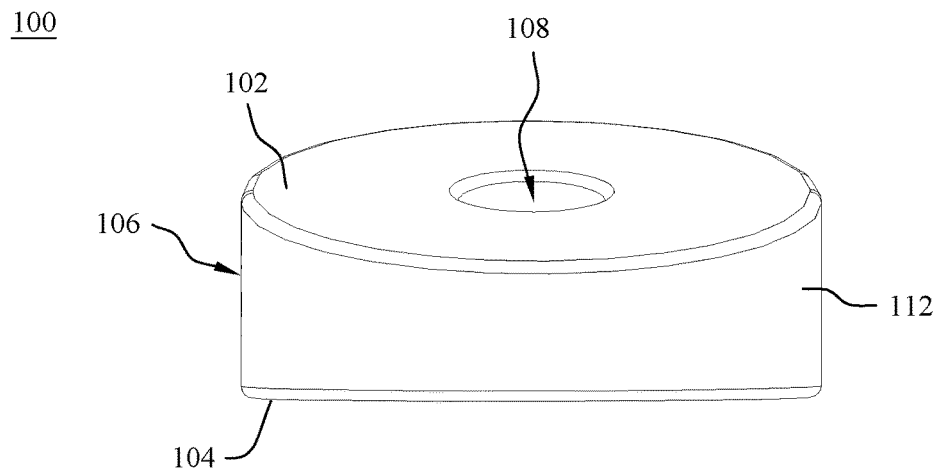
FIG. 2 is a rear view of the trial insert of FIG. 1, in accordance with an aspect of the present invention.

The trial insert 100 may also include a central mark 114, for example, the central mark or notch 114 may be numbered "0", as shown in FIGS. 1 and 3-5. In addition, the trial insert 100 may include at least one second mark 116, 118 and at least one third mark 120, 122. The at least one second mark 116, 118 may be, for example, a right second mark 116 positioned to the right of the center mark 114 and a left second mark 118 positioned to the left of the center mark 114. The at least one second mark 116, 118, as shown in FIGS. 1 and 3-5, may be numbered "3" and designate a 45° angle from the central mark 114. The at least one third mark 120, 122 may be, for example, a right third mark 120 positioned to the right of the center mark 114 and the right second mark 116 and a left third mark 122 positioned to the left of the center mark 114 and the left second mark 118. The at least one third mark 120, 122, as shown in FIGS. 1, 3 and 5, may be numbered "6" and designate a 90° angle from the central mark 114. In addition, the trial insert 100 may include additional markings 124 positioned between each of the central mark 114, the at least one second mark 116, 118 and the at least one third mark 120, 122. Each of the additional markings 124 may designate, for example, a 15° angle between the adjacent marks. The central mark 114, at least one second mark 116, 118, at least one third mark 120, 122 and the markings 124 may be, for example, markings on the exterior surface of the trial insert 100 or may alternatively be notches or grooves inset into the trial insert 100 from the exterior surface. The trial insert 100 may also include, for example, a first hole 110 positioned between the central mark 114 and the right second mark 116, a second hole 110 positioned between the central mark 114 and the left second mark 118, a third hole 110 positioned between the right second mark 116 and the right third mark 120, and a fourth hole 110 positioned between the left second mark 118 and the left third mark 122.

Figure 6:
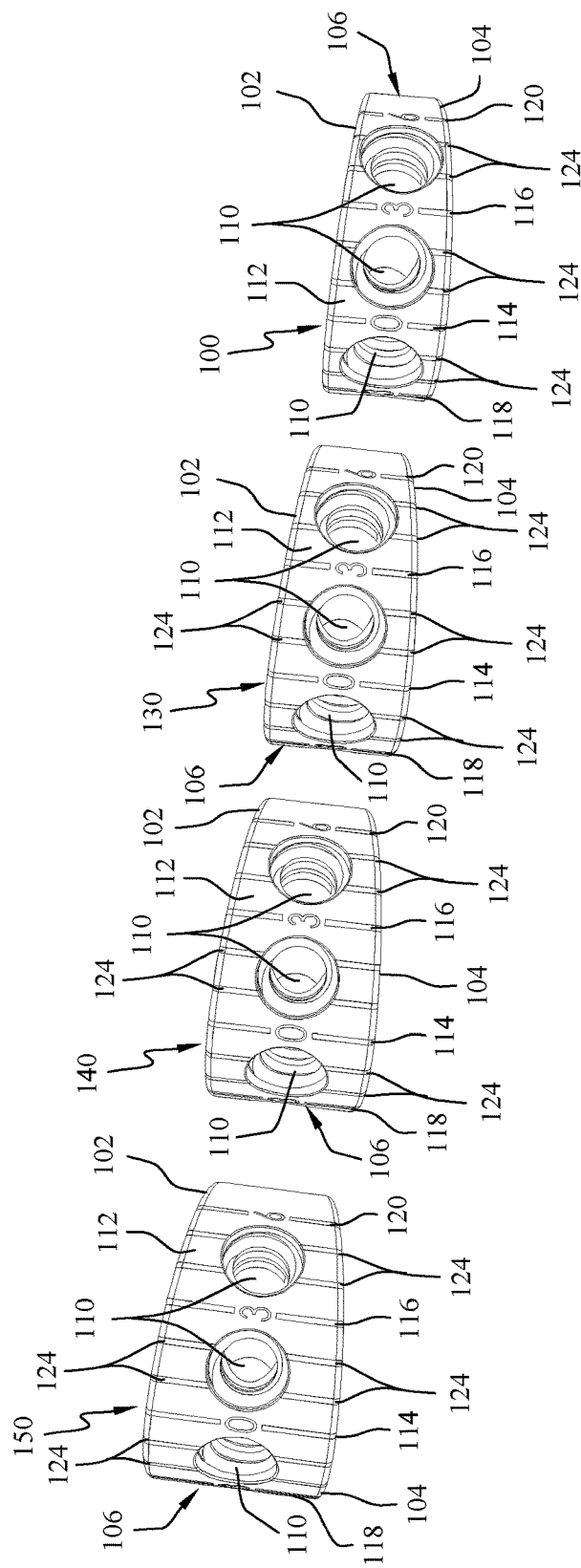
FIG. 6 is a side perspective view of a set of trial inserts, in accordance with an aspect of the present invention.

Referring now to FIG. 6, a set of trial inserts is shown. The set of trial inserts may include, for example, a first trial insert 100, a second trial insert 130, a third trial insert 140, and a fourth trial insert 150. The trial inserts 130, 140, 150 may be as described above with reference to trial insert 100 which will not be described again here for brevity sake. Each of the trial inserts 100, 130, 140, 150 may have a different width between the top surface 102 and the bottom surface 104.

Figure 7:
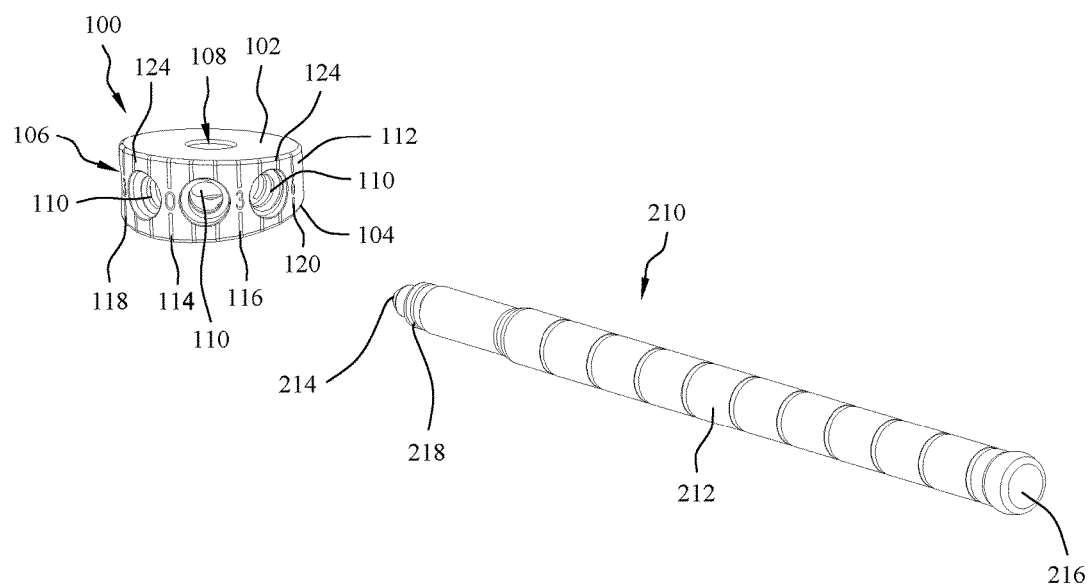
FIG. 7 is an exploded perspective view of a trial inserter system including the trial insert of FIG. 1 and the trial handle, in accordance with an aspect of the present invention.
Figure 8:
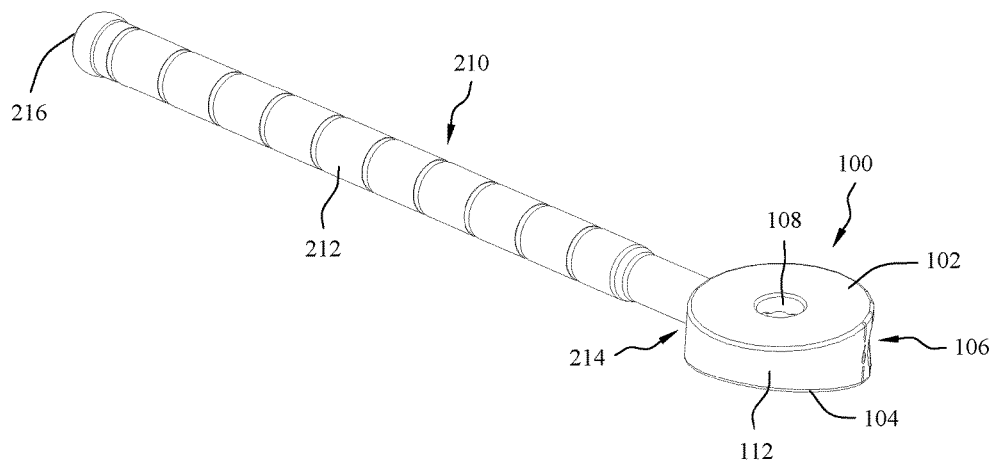
FIG. 8 is a rear perspective view of the trail inserter system of FIG. 7, in accordance with an aspect of the present invention.
Figure 9:
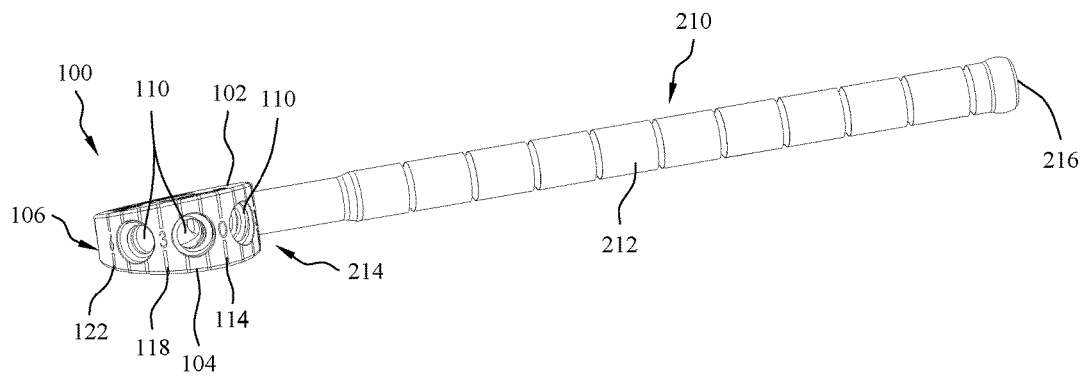
FIG. 9 is a front perspective view of the trial inserter system of FIG. 7, in accordance with an aspect of the present invention.
Figure 10:
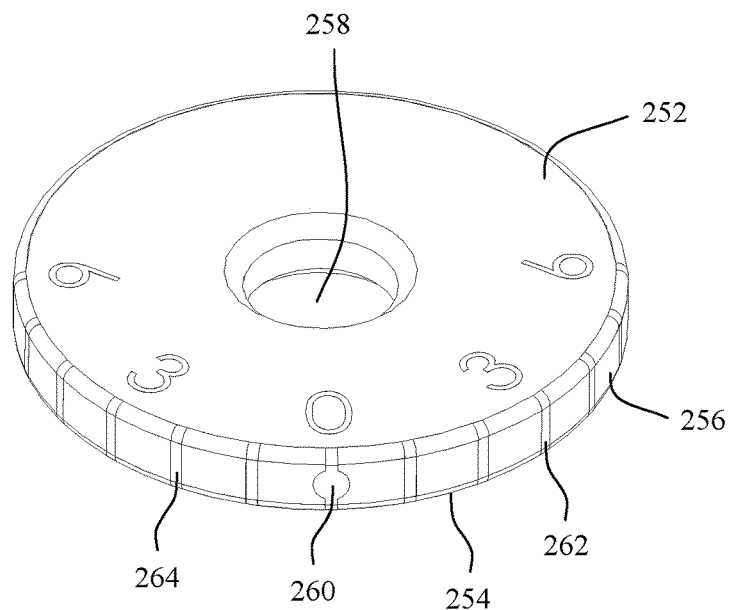
FIG. 10 is a perspective view of a correction indication guide, in accordance with an aspect of the present invention.
Figure 11:
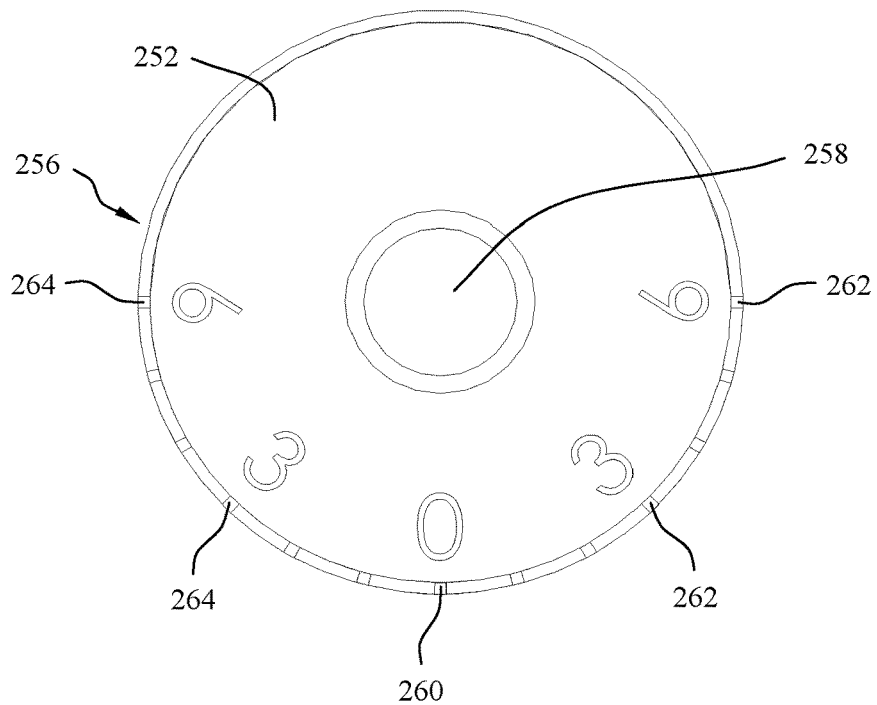
FIG. 11 is a top view of the correction indication guide of FIG. 10, in accordance with an aspect of the present invention.
Figure 12:
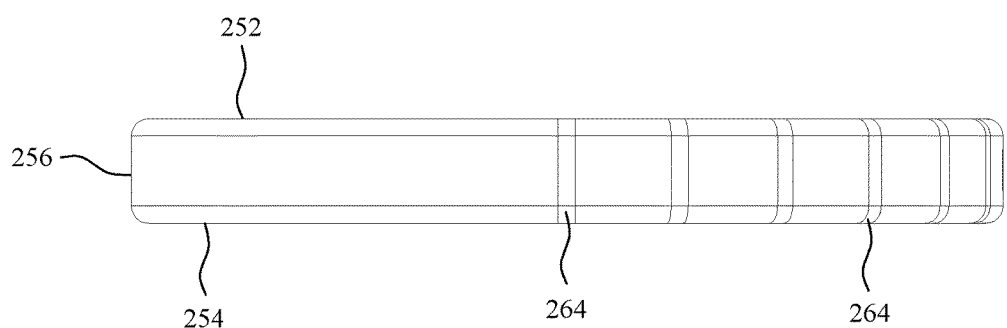
FIG. 12 is a first side view of the correction indication guide of FIG. 10, in accordance with an aspect of the present invention.
Figure 13:
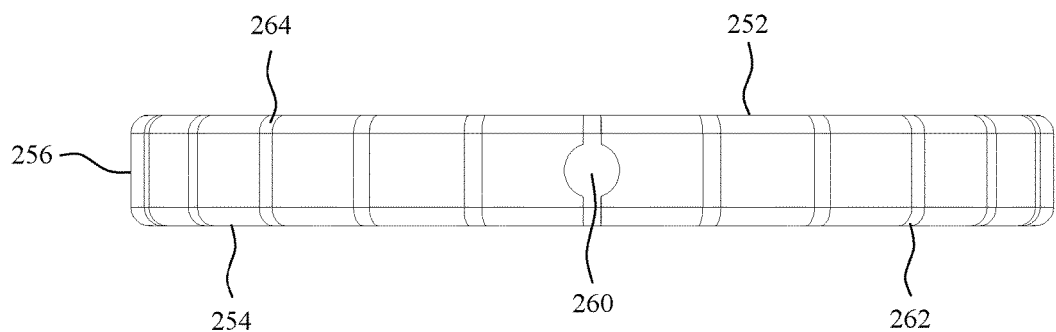
FIG. 13 is a front view of the correction indication guide of FIG. 10, in accordance with an aspect of the present invention.
Figure 14:
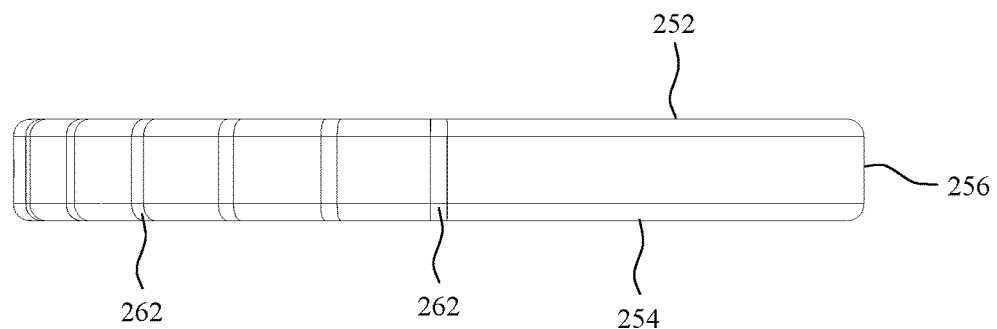
FIG. 14 is a second side view of the correction indication guide of FIG. 10, in accordance with an aspect of the present invention.
Figure 15:
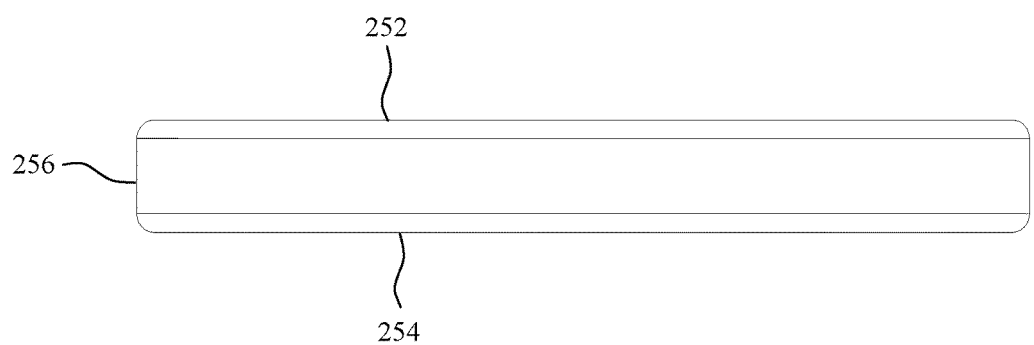
FIG. 15 is a rear view of the correction indication guide of FIG. 10, in accordance with an aspect of the present invention.

A trial inserter system 200 is shown in FIGS. 7-9. The trial inserter system 200 may include at least one trial insert 100, 130, 140, 150 and a handle 210. The at least one trial insert 100, 130, 140, 150 may be as described in greater detail above with reference to FIGS. 1-6, which will not be described again here for brevity sake. The handle 210 may include a body portion 212 with a first end 214 and a second end 216. The first end 214 of the body portion 212 may include a threaded portion 218. The threaded portion 218 may be, for example, sized and threaded to engage the holes 110 of the at least one trial insert 100, 130, 140, 150.

Referring now to FIGS. 10-15, a correction indication guide 250 is shown. The correction indication guide or coin correction indication guide 250 may include a top surface 252, a bottom surface 254, and an exterior surface 256 extending between the top surface 252 and a bottom surface 254. The correction indication guide 250 may include an opening 258 extending between the top surface 252 and the bottom surface 254. In addition, the correction indication guide 250 may include a middle marking 260 positioned on the exterior surface 256. The middle marking 260 may be, for example, labeled with the number "0" or other distinctive marking or surface notch. The correction indication guide 250 may also include a plurality of right markings 262 positioned to the right of the middle marking 260 and a plurality of left markings 264 positioned to the left of the middle marking 260. The plurality of right markings 262 may include, for example, a marking corresponding to the position of the right second mark 116 of the trial insert 100 and another marking corresponding to the position of the right third mark 120 of the trial insert 100. The plurality of markings 264 may include, for example, a marking corresponding to the position of the left second mark 118 of the trial insert 100 and another marking corresponding to the position of the left third mark 122 of the trial insert 100.

Figure 16:
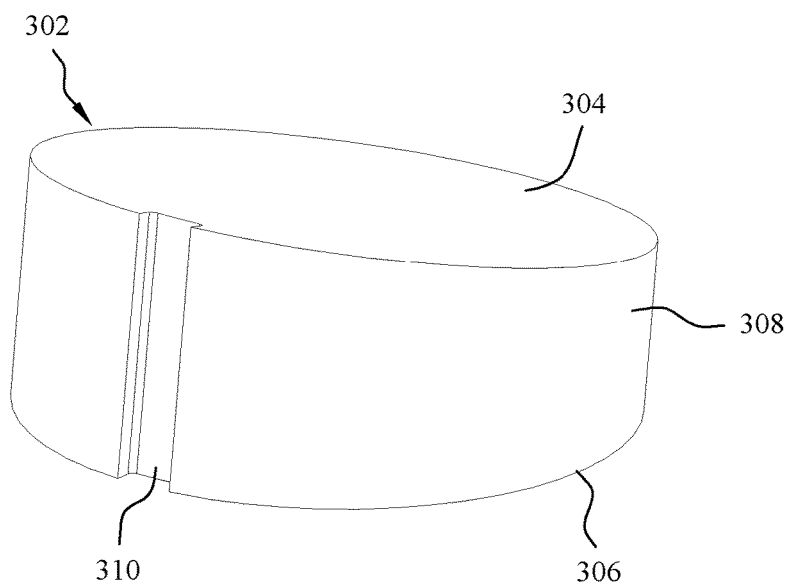
FIG. 16 is a perspective view of an implant, in accordance with an aspect of the present invention.
Figure 17:
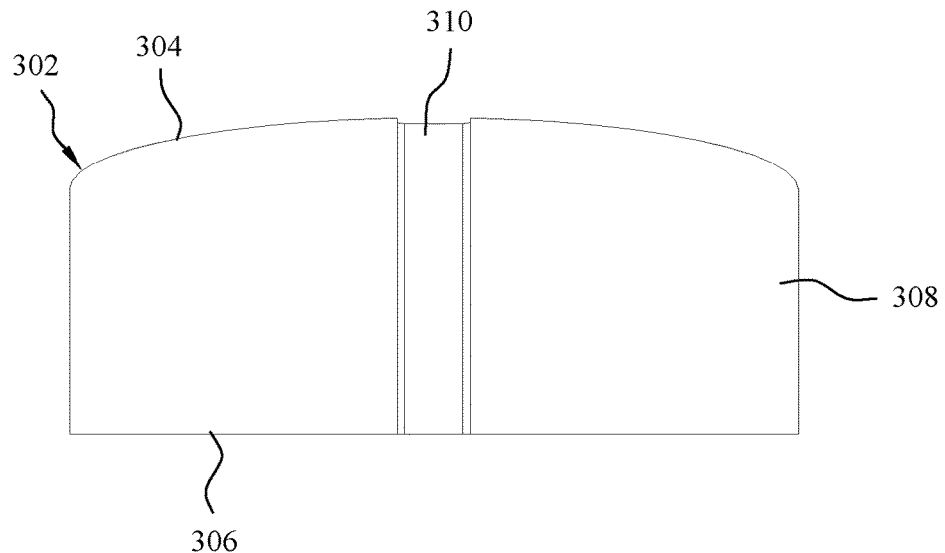
FIG. 17 is a front view of the implant of FIG. 16, in accordance with an aspect of the present invention.
Figure 18:
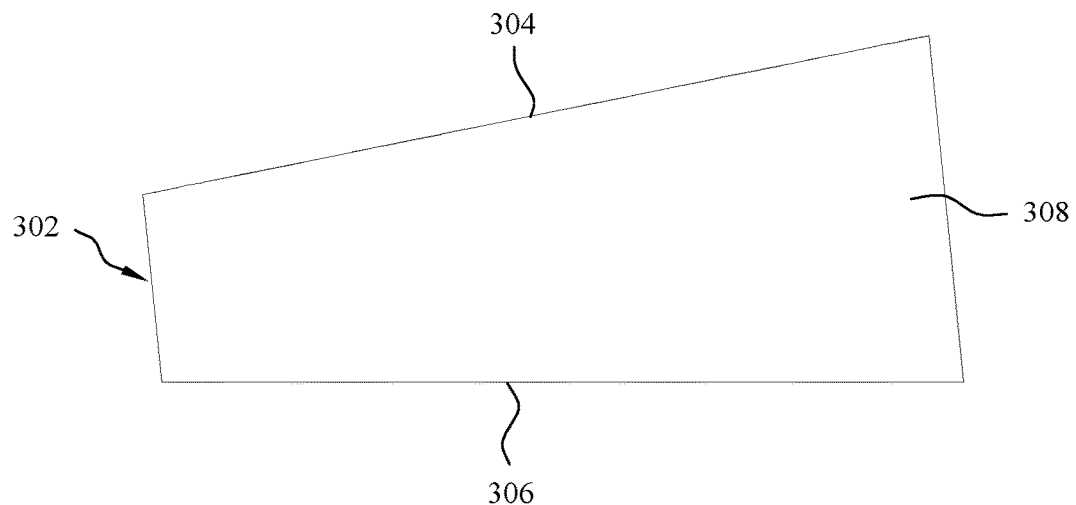
FIG. 18 is a side view of the implant of FIG. 16, in accordance with an aspect of the present invention.
Figure 19:
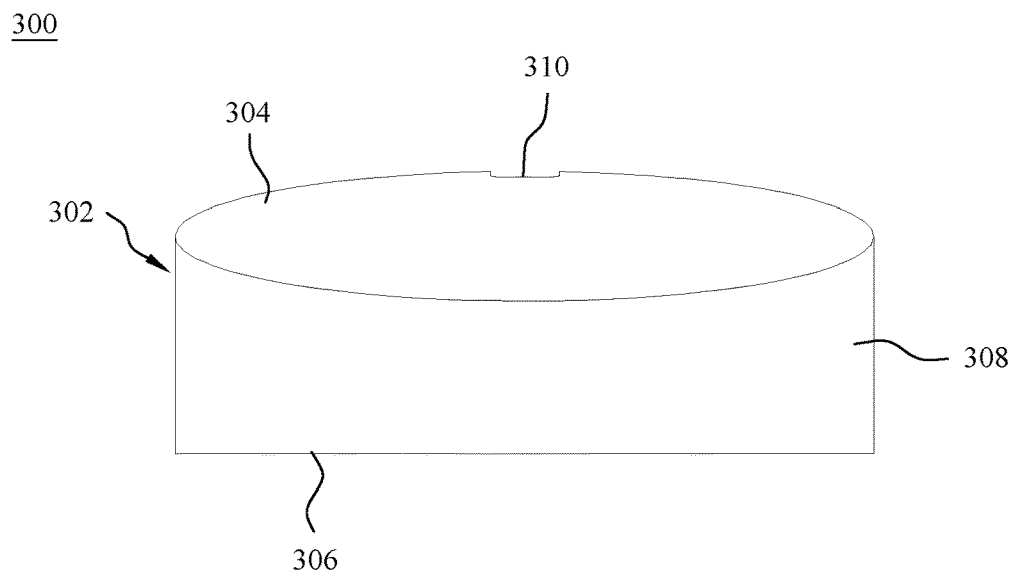
FIG. 19 is a rear view of the implant of FIG. 16, in accordance with an aspect of the present invention.
Figure 20:
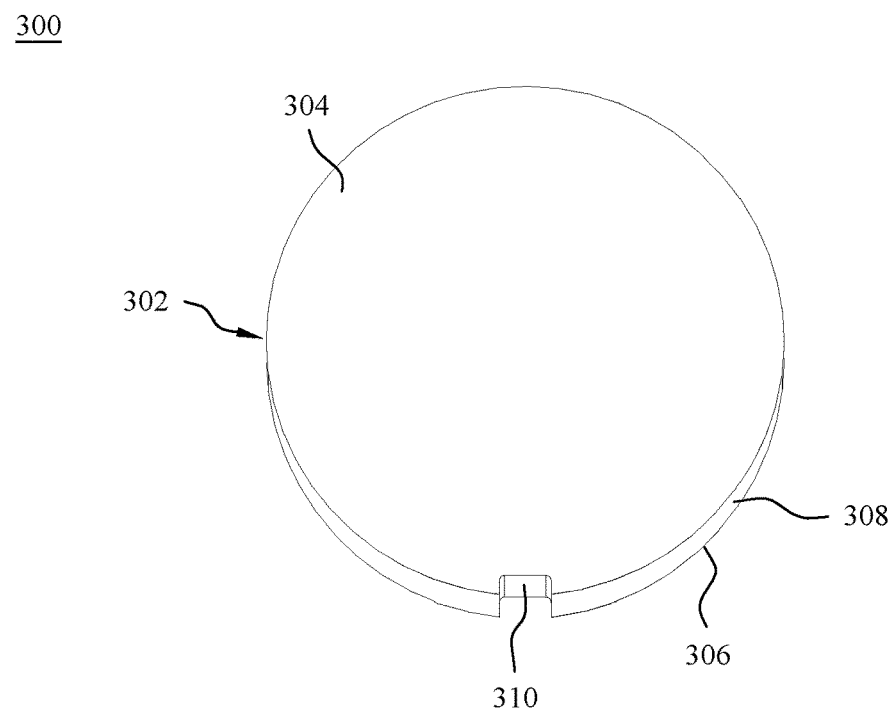
FIG. 20 is a top view of the implant of FIG. 16, in accordance with an aspect of the present invention.

An implant 300 is shown in FIGS. 16-20. The implant 300 may include a body 302 with a top surface 304, a bottom surface 306, and an exterior side surface 308. The top surface 304 may be, for example, angled with respect to the bottom surface 306, as shown in FIGS. 16, 18 and 19. In alternative embodiments, the top surface may be, for example, planar with respect to the bottom surface 306. The implant 300 may also include a recessed region 310 positioned in the exterior side surface 308 of the body 302. The recessed region 310 may correspond to, for example, the central mark 114 on the selected trial insert 100, 130, 140, 150.

Figure 21:
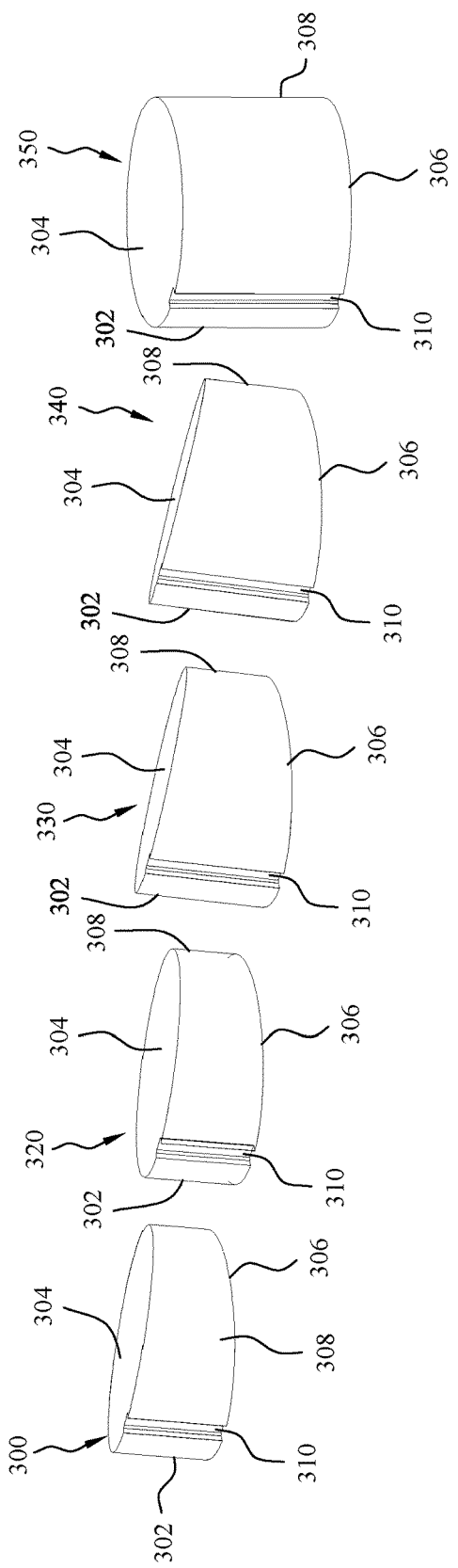
FIG. 21 is a perspective view of a set of implants, in accordance with an aspect of the present invention.

Referring now to FIG. 21, a set of implants is shown. The set of implants may include, for example, a first implant 300, a second implant 320, a third implant 330, a fourth implant 340, and a fifth implant 350. The implants 320, 330, 340 may be as described above with reference to implant 300 which will not be described again here for brevity sake. Each of the implants 300, 320, 330, 340 may have a different width between the top surface 304 and the bottom surface 306. The implant 350 may have, for example, a body 302 with a top surface 304 that is planar with the bottom surface 306 and an exterior side surface 308 extending between the top surface 304 and the bottom surface 306. The implant 350 may also include a recessed region 310 positioned in the exterior side surface 308 of the body 302. The recessed region 310 may correspond to, for example, the central mark 114 on the selected trial insert 100, 130, 140, 150. The size and shape of the implants 300, 320, 330, 340 may, for example, correspond to the sizes and shapes of the trial inserts 100, 130, 140, 150, respectively. Specifically, the width and slope of the top surface of the implants 300, 320, 330, 340 may correspond to the width and slope of the top surface of the trial inserts 100, 130, 140, 150. The implants 300, 320, 330, 340 may be made of, for example, titanium, poly-ether-ether-ketone, an additively manufactured material, or the like.

The set of trial inserts 100, 130, 140, 150, at least one handle 210, correction indication guide 250 and set of implants 300, 320, 330, 340, 350 may be packaged in a kit for use during a subtalar distraction arthrodesis procedure.

Figure 22:
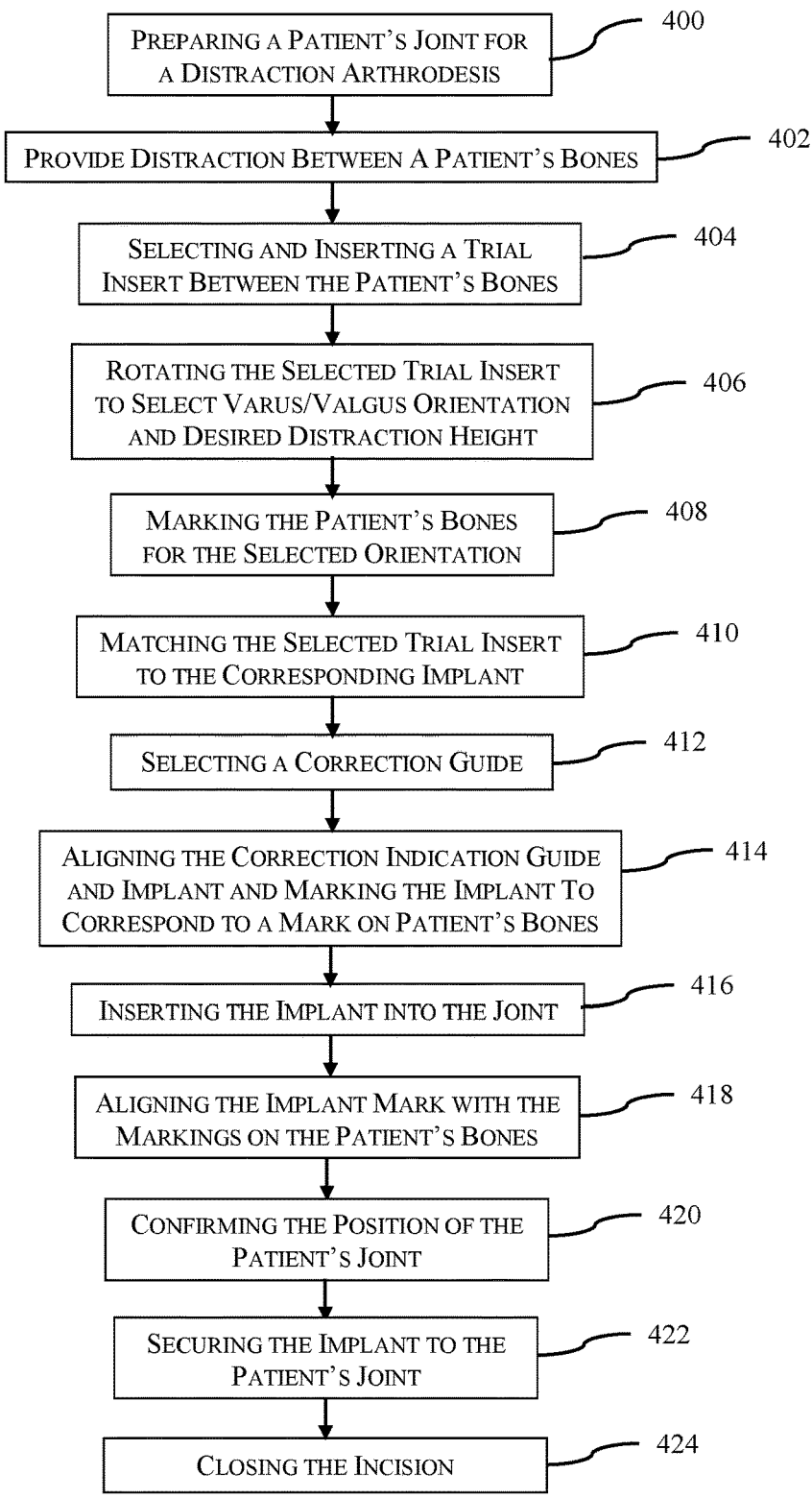
FIG. 22 depicts one embodiment of a surgical method for performing a subtalar distraction arthrodesis, in accordance with an aspect of the present invention.
Figure 23:
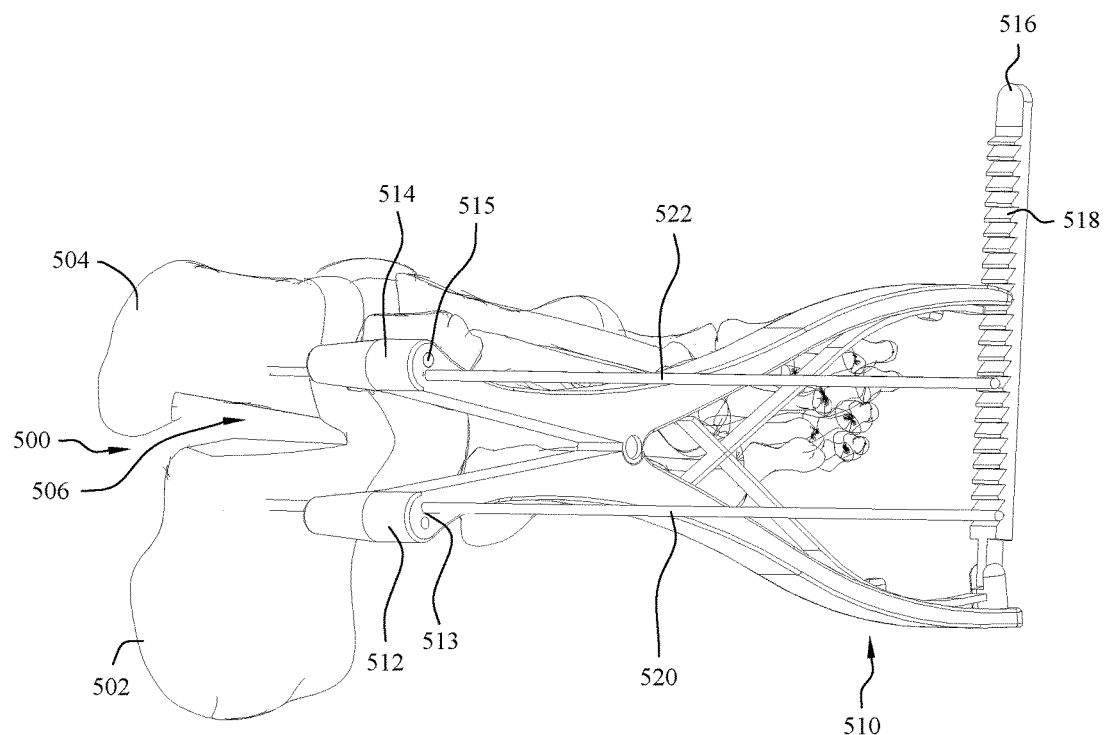
FIG. 23 is a perspective view of a foot and a retractor device, in accordance with an aspect of the present invention.

A surgical method of using the set of trial inserts 100, 130, 140, 150, at least one handle 210, correction indication guide 250 and set of implants 300, 320, 330, 340, 350 is shown in FIG. 22. The method may include, for example, preparing a patient's joint for a distraction arthrodesis 400 by providing distraction between a patient's bones 402. The method may also include selecting and inserting a trial insert between the patient's bones 404 and rotating the selected trial insert to select a varus/valgus orientation and a desired distraction height 406. The terms "distraction height" and "distraction distance" may be used herein interchangeable as they each refer to the space between the patient's bones 402, 404 after a distraction is performed. In addition, the method may include marking the patient's bones for the selected orientation 408 and matching the selected trial insert to the corresponding implant 410. The method may further include selecting a correction indication guide 412 and aligning the correction indication guide with the implant, then marking the implant using the correction indication guide to match the desired orientation marking on the patient's bones 414.

The method may also include inserting the implant between the patient's bones 416 and aligning the implant mark with the marking on the patient's bones 418. In addition, the method may include confirming the position of the patient's joint 420 and securing the implant to the patient's joint 422. Finally, the method may include closing the patient's incision 424.

Referring now to FIGS. 23-26, one embodiment of the surgical method is described in greater detail. First, the patient's joint 500 may be prepared for a distraction arthrodesis. The distraction arthrodesis may be performed alone or in combination with other procedures including, for example, a Dwyer closing wedge osteotomy for varus malalignment, a medial displacement calcaneal osteotomy for valgus mal-alignment, or a lateral wall exostectomy. If the patient has existing hardware positioned such that it may interfere with the distraction arthrodesis procedure, the existing hardware may be removed. The patient's joint 500 may then be prepared by making an incision to expose the patient's joint 500. The position of the incision may be selected based on concomitant procedures, previous incisions, and/or hardware removal considerations. In one embodiment, the incision may be made from a lateral decubitus position and carried down to the subtalar joint. Fluoroscopy may optionally be used while making the incision. Next, the joint may be prepared by exposing the subtalar joint to provide adequate visualization of the posterior facet. In addition, the calcaneofibular ligament may be released and the peroneal tendons mobilized to retract them away from the surgical site.

After the subtalar joint is mobilized, a distractive force may be provided between the patient's bones. In one embodiment, as shown in FIGS. 23-26, a retractor 510, for example, a Hintermann retractor may be coupled to the bones 502, 504 of the patient's subtalar joint 500. The retractor 510 may include a first arm 512 hingedly coupled to a second arm 514 near a mid-point of the arms 512, 514. The retractor 510 may also include a ratchet arm 516 coupled to a second end of the first arm 512. The ratchet arm 516 may include teeth 518 sized and shaped to receive a second end of the second arm 514. The first end of the first arm 512 may include at least one opening 513 for receiving, for example, a guide wire or k-wire, and the first end of the second arm 514 may include at least one opening 515 for receiving, for example, a guide wire or k-wire. The first arm 512 of the retractor 510 may be coupled to the calcaneus bone 502 with a k-wire 520 and the second arm 514 of the retractor 510 may be coupled to the talus bone 504 with a k-wire 522. Once the k-wires 520, 522 are inserted into the patient's bones 502, 504, the retractor 510 may be used to distract the subtalar joint 500. The retractor 510 may distracted until a desired opening 506 is achieved in the subtalar joint 500 between the bones 502, 504. The ratchet arm 516 of the retractor 510 may hold the subtalar joint 500 open to maintain the desired opening 506 during the procedure. Once the subtalar joint 500 is distracted, cartilage resection may be performed on either side of the posterior facet of the subtalar joint 500. In addition, if desired, cartilage resection may be performed off the anterior and middle facets.

Optionally, a flat surface may now be obtained on the posterior facet of the talus 504 and calcaneus 502. Alternatively, the flat surfaces of the posterior facet of the talus 504 and calcaneus 502 may be obtained during a later step of the surgical procedure. In addition, if necessary, subchondral drilling or scraping of the surfaces of the bones 502, 504 may be performed.

Next, a trial insert 100, 130, 140, 150 should be selected and inserted between the patient's bones 502, 504. A first trial insert, for example, trial insert 100 may be selected and coupled to the handle 210, for example, as shown in FIGS. 8 and 9. The hole 110 for inserting the handle 210 may be chosen based on the position of the incision, which allows for the greatest rotational movement of the trial insert 100. For example, the hole 110 that positions the handle 210 in the most lateral and central position in the incision may be selected. Once the handle 210 is secured to the trial insert 100, the insert 100 may be introduced into the opening 506 of the subtalar joint 500. The insert 100 may be inserted, for example, closest to the posterior pathway as possible. In addition, the tallest portion of the insert 100, for example, the part of the insert 100 at the central mark 114, may be oriented posteriorly during insertion. After the insert 100 is positioned within the subtalar joint 500, the distraction height of the insert 100 between the bones 502, 504 may be determined. If the insert 100 does not fit snugly or to the satisfaction of the practitioner, the insert 100 may be removed and a larger insert 130, 140, 150 may be selected, attached to the handle 210 and inserted between the bones 502, 504. The larger insert 130, 140, 150, for example, the insert 130 may be attached to the handle 210, such that the handle 210 is attached laterally on the insert 130 and inserted, such that tallest portion of the insert 130 is oriented posteriorly. If insert 130 does not fit snugly between the bones 502, 504, then insert 130 may be removed and a larger insert 140, 150 may be attached to the handle 210 and inserted into the opening 506. The inserts 100, 130, 140, 150 may be selected until the implant 100, 130, 140, 150 with the correct distraction height is obtained to allow for the desired correction in the sagittal plane.

Figure 24:
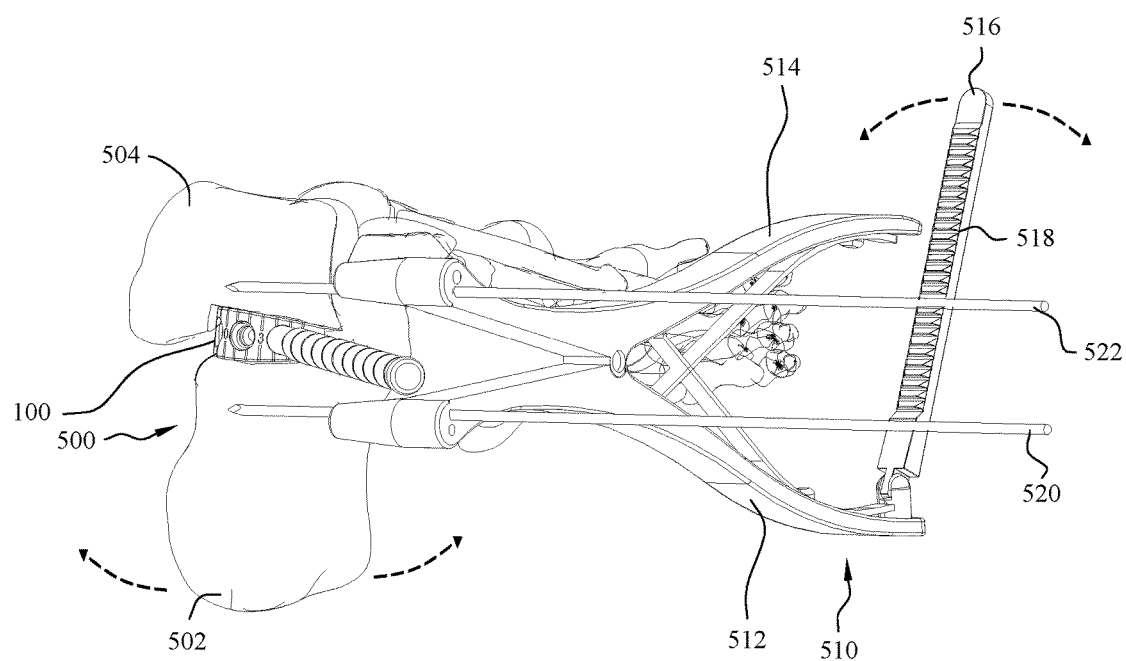
FIG. 24 is a perspective view of the foot and retractor device of FIG. 23 with a trial inserter system inserted into the patient's foot, in accordance with an aspect of the present invention.

When the correct size insert 100, 130, 140, 150 is obtained, the ratchet arm 518 may be rotated away from the second arm 514 of the retractor 510 to allow the calcaneus bone 502 to move freely in varus and valgus until the desired valgus/varus orientation of the calcaneus bone 502 is achieved in the frontal plane, as shown in FIG. 24. If the desired reduction of the calcaneus 502 cannot be achieved with the selected trial insert 100, then a larger trial insert 130, 140, 150 may be selected and inserted to allow for additional reduction of the calcaneus 502. Once the desired bi-planar correction, i.e., height and varus/valgus orientation, of the calcaneus 502 is achieved with the trial insert 100, 130, 140, 150, then at least one of the patient's bones 502, 504 may be marked or scored using a marker or bovie. The mark should be made to correspond to at least one of the marks 114, 116, 118, 120, 122 on the trial insert 100, 130, 140, 150 positioned within the bones 502, 504. The at least one mark on the bone 502, 504 is preferably clearly visible through the patient's incision. In addition, the number corresponding to the selected mark 114, 116, 118, 120, 122 should be noted for later insertion of the implant 300. In addition, now that the trial insert 100, 130, 140, 150 is selected, the insert 100, 130, 140, 150 may optionally be used as a cut guide to create flat surfaces on the bones 502, 504. Once the position has been achieved and the bone has been marked, the ratchet arm 518 is rotated back to engage with the second arm 514 of the retractor 510 to hold this position open.

Figure 25:
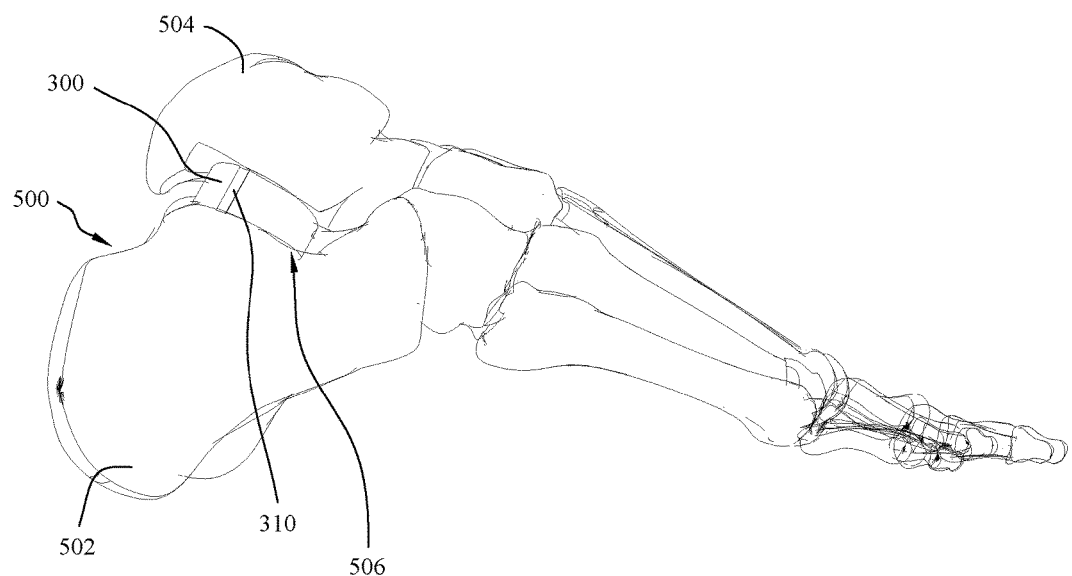
FIG. 25 is a perspective view of the foot of FIG. 23 and an implant inserted into the foot, in accordance with an aspect of the present invention.
Figure 26:
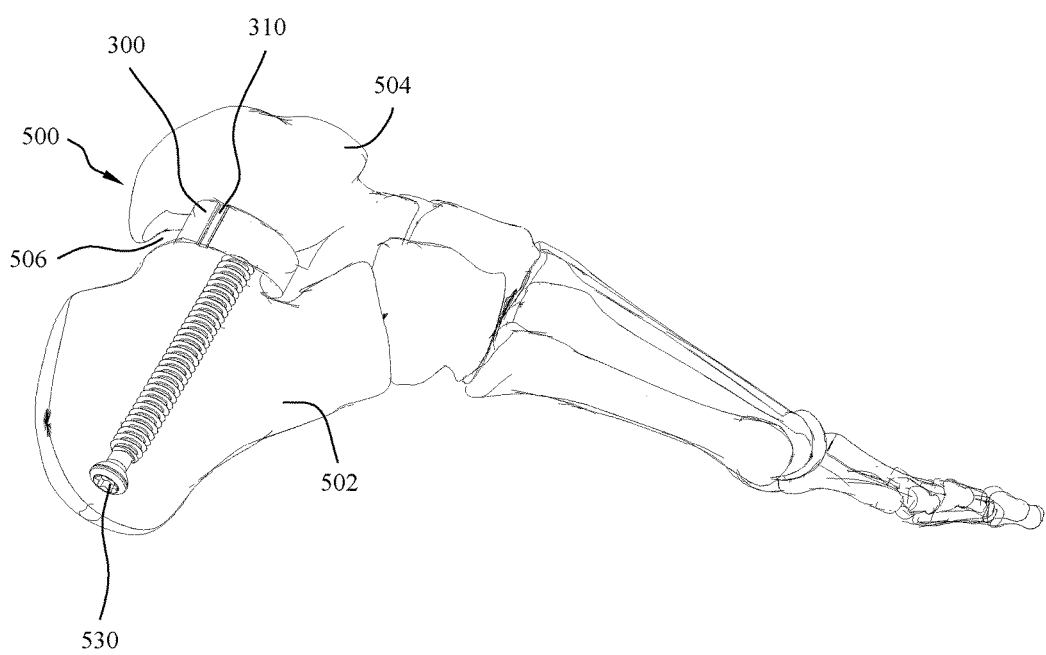
FIG. 26 is a perspective view of the foot and implant of FIG. 25 with a fastener inserted into the foot through a transparent calcaneus, in accordance with an aspect of the present invention.

Next, an implant 300, 320, 330, 340, 350 may be selected based on the selected trial insert 100, 130, 140, 150. The implant 300, 320, 330, 340, 350 that is selected should correspond to the selected trial insert 100, 130, 140, 150. As illustrated in FIG. 25, the implant 300 may be selected as it corresponds with trial insert 100. The implants 300, 320, 330, 340, 350 may be, for example, a bone graft. If a bone graft is used, it should be prepared using any known procedures, for example, hydration in normal sterile saline. In addition, the implant 300, 320, 330, 340, 350 may be, for example, treated with platelet rich protein, blood, bone marrow aspirate, or other osteogenic medium as desired to improve graft incorporation.

A correction indication guide 412 may then be placed on top of the implant 300. The recessed region 310 of the implant 300 being aligned with the middle marking or zero marking 260 of the correction indication guide 412. With the zero marking 260 and recessed region 310 aligned, the implant 300 may be marked or scored using a marker or bovie at the mark 114, 116, 118, 120, 122, 124 which corresponds to the mark made on the patient's bones 502, 504 with the trial insert 100. Once the implant 300 is marked, the implant 300 may be inserted into the opening 506 of the subtalar joint 500, as shown in FIG. 25. The mark on the implant 300 is then aligned with the marks on at least one of the patient's bones 502, 504. If needed, a bone tamp may be used to fully seat the implant 300 into the opening 506 between the bones 502, 504. After the implant 300 is fully inserted, the reduction of the bones 502, 504 may be confirmed, for example, using fluoroscopy.

Next, the implant 300 may be fixed to the bones 502, 504. For example, the implant 300 may be temporarily fixed using at least one k-wire or guide wire. The k-wire may be inserted into, for example, a posterior aspect of the heel above the weight bearing surface, through the calcaneus 502, across the implant 300, and into the talus 504. After insertion of the k-wire the reduction of the subtalar joint 500 may be confirmed again using, for example, fluoroscopy. Once the temporary fixation is achieved, permanent fixation may be performed. The permanent fixation may include inserting a screw 530 through the calcaneus 502, across the implant 300, and into the talus 504. It is preferred that a screw 530 that will maintain the correction and provide fixation without providing excessive compression across the implant 300 is used. To insert the screw 530, a guide with soft tissue protection may be used. The insertion of the screw 530 may include drilling over the guide wire (not shown). Optionally, a depth gauge may be used to select the length of the screw 530. If the screw 530 is to be countersunk, the countersink drill may be inserted over the guide wire (not shown) and countersinking may be performed. After all drilling is complete, the screw 530 may be inserted over the guide wire. Once inserted the position and length of the screw 530 may be confirmed, for example, using fluoroscopy. Once the position and length of the screw 530 are confirmed, the guide wire (not shown) may be removed from the patient's bones 502, 504. Then, the concomitant procedures may be performed and the incision closed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A distraction kit, comprising:
    at least one trial insert, wherein the at least one trial insert comprises:
        a top surface;
        a bottom surface;
        a body portion extending between the top surface and the bottom surface;
        at least one hole extending from an exterior surface of the body portion toward a center of the at least one trial insert;
        a central mark;
        at least one second mark positioned adjacent to the central mark; and
        at least one third mark positioned adjacent to the at least one second mark;
        wherein the top surface is angled with respect to the bottom surface;
    at least one handle for coupling to the at least one trial insert via the at least one hole;
    a correction indication guide, wherein the correction indication guide comprises:
        at least one marking, wherein the at least one marking corresponds to at least one of the central mark, the at least one second mark and the at least one third mark of the at least one trial insert; and
    at least one implant.

2. The distraction kit of claim 1, wherein the at least one second mark further comprises:
    a right second mark positioned adjacent to the central mark on the right side;
    a left second mark positioned adjacent to the central mark on the left side; and
    wherein the at least one third mark comprises:
    a right third mark positioned adjacent to the right second mark on the right side of the central mark; and
    a left third mark positioned adjacent to the left second mark on the left side of the central mark.

3. The distraction kit of claim 2, wherein the at least one hole is four holes.

4. The distraction kit of claim 3, wherein a first hole is positioned between the central mark and the right second mark, a second hole is positioned between the central mark and the left second mark, a third hole is positioned between the right second mark and the right third mark, and a fourth hole is positioned between the left second mark and the left third mark.

5. The distraction kit of claim 4, wherein the first hole, the second hole, the third hole and the fourth hole are threaded.

6. The distraction kit of claim 1, wherein the at least one implant comprises:
    a body comprising:
        a top surface;
        a bottom surface;
        an exterior side surface extending between the top surface and the bottom surface; and
        a recessed region positioned in the exterior side surface, wherein the recessed region corresponds to the central mark of the at least one trial insert and wherein the recessed region corresponds to at least one of the at least one markings of the correction indication guide.

7. The distraction kit of claim 6, wherein the top surface of the at least one implant is angled with respect to the bottom surface.

8. The distraction kit of claim 6, wherein the top surface and bottom surface of the at least one implant are planar relative to each other.

9. The distraction kit of claim 6, wherein the recessed region extends from the top surface to the bottom surface in the exterior side surface.

10. The distraction kit of claim 1, wherein the at least one handle comprises:
    a body portion with a first end and a second end; and
    a threaded portion at the first end, wherein the threaded portion is formed to couple to the at least one trial insert.

11. The distraction kit of claim 10, wherein the body portion of the at least one handle is elongated and cylindrically shaped.

12. The distraction kit of claim 1, wherein the at least one trial insert further comprises:
    at least one opening extending between the top surface and the bottom surface and passing through the body portion.

13. The distraction kit of claim 12, wherein the at least one opening is positioned in a center region of the top surface and in a center region of the bottom surface.

14. The distraction kit of claim 1, wherein the at least one handle is configured to directly couple to the at least one hole.

15. A distraction kit, comprising:
    at least one trial insert;
    at least one handle for coupling to the at least one trial insert;
    a correction indication guide, wherein the correction indication guide comprises:
        a top surface;
        a bottom surface opposite the top surface;
        an exterior surface extending between the top surface and the bottom surface; and
        at least one marking positioned on the exterior surface; and
        wherein the correction indication guide has a circular cross-sectional shape and a shape of the exterior surface of the correction indication guide corresponds to a shape of an exterior surface of the at least one trial insert; and
    at least one implant.

16. The distraction kit of claim 15, wherein the at least one marking of the correction indication guide comprises:
    a middle marking;
    a plurality of right markings positioned to the right of the middle marking; and
    a plurality of left markings positioned to the left of the middle marking.

17. The distraction kit of claim 15, wherein the correction indication guide further comprises an opening, wherein the opening extends from the top surface through the bottom surface.

* * * * *